United States Patent
Snyder et al.

(10) Patent No.: US 7,360,537 B2
(45) Date of Patent: Apr. 22, 2008

(54) ANTISTATIC MEDICATION DELIVERY APPARATUS

(75) Inventors: Sarah Bruce Snyder, Waterloo (CA); James N. Schmidt, London (CA)

(73) Assignee: Trudell Medical International, London, Ontario (CA)

( * ) Notice: Subject to any disclaimer, the term of this patent is extended or adjusted under 35 U.S.C. 154(b) by 139 days.

(21) Appl. No.: 10/821,260

(22) Filed: Apr. 8, 2004

(65) Prior Publication Data

US 2005/0005929 A1    Jan. 13, 2005

Related U.S. Application Data

(60) Provisional application No. 60/463,288, filed on Apr. 16, 2003.

(51) Int. Cl.
*A61M 11/00* (2006.01)
*A61M 15/00* (2006.01)

(52) U.S. Cl. .............................. 128/200.23; 128/203.15
(58) Field of Classification Search ........... 128/200.23, 128/203.12, 200.14, 203.15, 203.19, 203.21
See application file for complete search history.

(56) References Cited

U.S. PATENT DOCUMENTS

| | | | |
|---|---|---|---|
| 3,896,101 A * | 7/1975 | McIntosh et al. ........... 524/251 |
| 4,509,515 A | 4/1985 | Altounyan et al. |
| 5,848,588 A | 12/1998 | Foley et al. |
| 5,881,718 A | 3/1999 | Mortensen et al. |
| 6,039,042 A | 3/2000 | Sladek |
| 6,293,279 B1 * | 9/2001 | Schmidt et al. ........ 128/200.23 |
| 6,345,617 B1 * | 2/2002 | Engelbreth et al. .... 128/200.23 |
| 6,435,176 B1 * | 8/2002 | Berg et al. ............. 128/200.23 |
| 6,557,549 B2 * | 5/2003 | Schmidt et al. ........ 128/200.24 |
| 6,848,443 B2 * | 2/2005 | Schmidt et al. ........ 128/200.23 |

(Continued)

FOREIGN PATENT DOCUMENTS

| | | | |
|---|---|---|---|
| WO | WO 93/11817 | * | 6/1993 |
| WO | WO 95/20414 | | 8/1995 |
| WO | WO 98/19727 A | | 5/1998 |
| WO | WO 02/04056 A | | 1/2002 |

(Continued)

OTHER PUBLICATIONS

Rupprect, L; Hawkinson C: "Conductive Plastics for Medical Applications," Medical Device & Diagnostic Industry, Jan. 1999 column, XP002286594, whole document.*

(Continued)

*Primary Examiner*—Teena Mitchell
(74) *Attorney, Agent, or Firm*—Brinks Hofer Gilson & Lione (57) ABSTRACT

An aerosol medication delivery apparatus include a holding chamber having an input end and an output end and defining an interior space. In one embodiment, the holding chamber is antistatic and is made of a plastic material having a surface resistivity of between about 10E10 and about 10E12 ohm/sq. In another embodiment, a component, such as a backpiece or mouthpiece, separate from the holding chamber, is antistatic and is made of a material having a surface resistivity of between about 10E10 and about 10E12 ohm/sq. The component is connected to the holding chamber, which may or may not be antistatic. In one embodiment, the component is made of an elastomeric material. In one embodiment, at least a portion of the holding chamber and/or component is see-through. Various methods for introducing an aerosol into the holding chamber at the input end thereof and inhaling the aerosol through the output end are also provided.

17 Claims, 6 Drawing Sheets

U.S. PATENT DOCUMENTS

| | | | |
|---|---|---|---|
| 7,013,896 B2* | 3/2006 | Schmidt | 128/206.15 |
| 7,022,764 B2 | 4/2006 | Murray | |
| 2003/0205226 A1 | 11/2003 | Gallem et al. | |
| 2004/0094148 A1* | 5/2004 | Lulla et al. | 128/200.23 |
| 2005/0039741 A1 | 2/2005 | Gallem et al. | |
| 2006/0011196 A2 | 1/2006 | Gallem et al. | |
| 2006/0254579 A1* | 11/2006 | Grychowski et al. | 180/200.22 |

OTHER PUBLICATIONS

International Search Report, mailed Aug. 12, 2004, PCT/IB2004/001132.

Written Opinion of the International Searching Authority, or the Declaration, mailed Aug. 12, 2004, PCT/IB2004/001132.

Rupprect, L; Hawkinson C: "Conductive Plastics for Medical Applications," Medical Device & Diagnostic Industry, 1999, XP002286594, p. 96—, whole document.

"Surface Resistivity" graph, origin and date unknown.

"Pharmaceutical Aerosol Systems Division AeroSpacer* Collapsible Integrated Actuator with AeroCount Integra* Integrated Dose Indicator," Trudell Medical International, TMI-Aerosol Pharma Systems—AeroSpacer web site, http://www.trudellmedical.com/aerosol_aerospacer_collapsible.shtml, Mar. 7, 2003, p. 1 of 2.

"Asthma COPD Products Home Page," Trudell Medical International, TMI-Asthma COPD Products website, http://www.trudellmedical.com/copd_home.shtml, Mar. 7, 2003, p. 1 of 2.

"Preliminary Product Data, PermaStat® 1500-50D Polyester Thermoplastic Elastomer (TPE) Permanently Anti-Static ESD Protection 50-A Durometer," RTP Imagineering Plastics®, RTP Company Product Data Sheet website, http://222.rtpcompany.com/info/data/1500/PermaStat1500-50D.htm, Mar. 7, 2003, pp. 1-2.

"Preliminary Product Data PermaStat® 1200-70A Polyurethane Thermoplastic Elastomer (TPU) Permanently Anti-Static ESD Protection 70-A Durometer," RTP Company Product Sheet website, http://www.rtpcompany.com/info/data/1200/PermaStat1200-70A.htm, Mar. 7, 2003, pp. 1-2.

"Preliminary Product Data RTP 199 X 92520 Polypropylene (PP) Long Glass Fiber Flame Retardant," RTP Company Product Data Sheet website, http://www.rtpcompany.com/info/data/0100/RTP199X92520.htm, Mar. 7, 2003, pp. 1-2.

"Preliminary Product Data PermaStat® 100 Polypropylene (PP) Permanently Anti-Static ESD Protection," RTP Company Product Data Sheet Website, http://www.rtpcompany.com/info/data/0100/PermaStat100.htm, Mar. 7, 2003, pp. 1-2.

"Preliminary Product Data PermaStat® 300 Polycarbonate (PC) Permanently Anti-Static ESD Protection," RTP Company Product Data Sheet website, http://www.rtpcompany.com/info/data/permastat/PermaStat300.htm, Mar. 7, 2003, pp. 1-2.

"Preliminary Product Data PermaStat® 600 Acrylonitrile Butadiene Styrene (ABS) Permanently Anti-Static ESD Protection," RTP Company Product Data Sheet website, http://www.rtpcompany.com/info/data/permastat/PermaStat600.htm, Mar. 7, 2003, pp. 1-2.

"Latest Innovations: Conductive Compounds, Typical conductive additives," RTP Company-Typical conductive additives—Conductive Compounds website, http://www.rtpcompany.com/products/conductive/additives.htm; copyright 1995-2003 RTP Company, Mar. 7, 2003, pp. 1-3.

"Latest Innovations: Elastomer Compounds," RTP Company—Thermoplastic Elastomer Compounds—Elastomer Compounds website, http://www.rtpcompany.com/products/elastomer/tpe.htm, copyright 1995-2003 RTP Company, Mar. 7, 2003, pp. 1-2.

"Latest Innovations: Conductive Compounds, PermaStat® Compounds," RTP Company—Permastat® Compounds—Conductive Compounds website, http://www.rtpcompany.com/products/conductive/permastat.htm, copyright 1995-2003 RTP Company, Mar. 7, 2003, pp. 1-3.

"PermaStat® Compounds," RTP Company—PermaStat® Compounds (Conductive)—Data Sheets website, http://www.rtpcompany.com/info/data/permastat/index.htm, copyright 1995-2001, Mar. 7, 2003, pp. 1-4.

* cited by examiner

ANTISTATIC MEDICATION DELIVERY APPARATUS

This application claims the benefit of U.S. Provisional Application Ser. No. 60/463,288, filed Apr. 16, 2003, the entire disclosure of which is hereby incorporated herein by reference.

BACKGROUND

The present invention relates to a medication delivery apparatus, and in particular, to an antistatic medication delivery apparatus.

Medication delivery systems are used, in general, to administer medication to a user. For example, aerosol delivery systems are configured to deliver a medication in aerosol form to the lungs of the user. Other systems deliver the medication to the nasal passageways of the user. Some systems use a pressurized metered-dose inhaler (pMDI), which typically includes a container in which medication particles are stored under pressure, and an actuator used to dispense the medication from the container.

In other systems, a holding chamber or spacer is connected to one of the container or actuator, as shown for example in U.S. Pat. No. 6,293,279, which is hereby incorporated herein by reference. The holding chamber reduces the need for the user to coordinate activation of the pMDI canister with inhalation, helps reduce the delivery of non-respirable medication particles from the canister, and helps reduce the impaction of medication particles in the user's oropharnyx and upper airway. In some configurations, shown for example in the U.S. Pat. No. 6,293,279 and U.S. Pat. No. 5,881,718, the apparatus can be provided with one or both of an inhalation and exhalation valve(s) at an output end of the chamber. The output end is typically configured with a mouthpiece, which is received in the mouth of the user, or with a mask, which is placed over the mouth and nose of the user.

Figure 8:
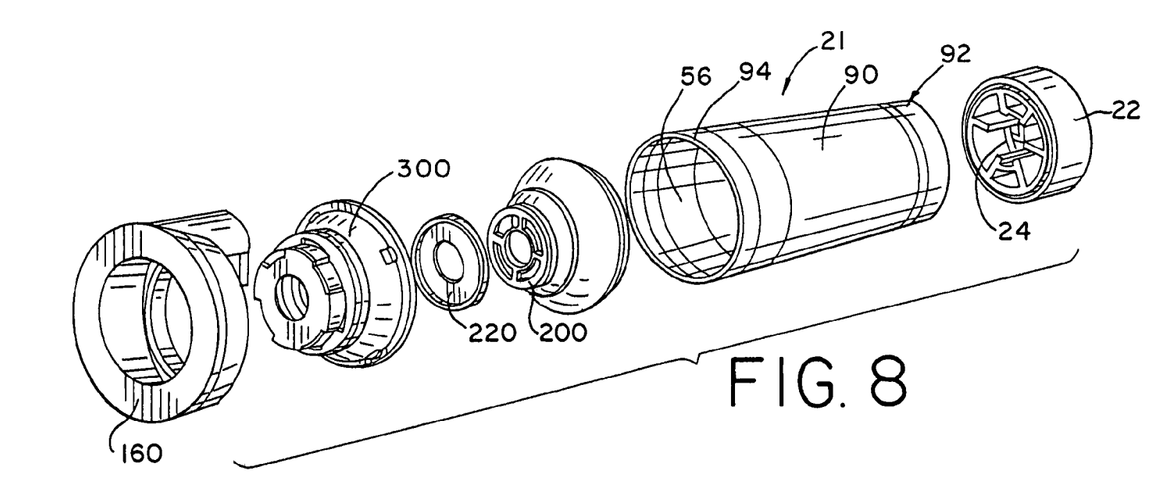

Often, holding chamber devices are made of various plastics, such as polypropylene or polycarbonates. However, plastic materials typically have relative high surface resistivities, typically greater than 10E12 ohm/sq. As such, the interior of the chamber can become electrostatically charged, thereby causing some of the medication particles in the aerosol to deposit on the walls and/or other parts attached to or forming part of the holding chamber. As disclosed in U.S. Pat. No. 6,435,176, for example, one solution to this problem is to provide a spacer made of metal or other materials having resistivities below 10E9 ohm. However, metal spacers or holding chambers, made for example of stainless steel or aluminum, are relatively expensive to manufacture and are heavy and more difficult to handle. In addition, metal spacers or holding chambers do not allow the user or caregiver to visualize the delivery of medication from the chamber. Likewise, many plastics, if formed with antistatic additives, such as metal fibers, are not see-through and can obstruct a view of the interior of the chamber. In addition, plastic components having an antistatic surface coating can tend to degrade and lose their antistatic properties over time, e.g., within about a year.

Another solution is to periodically wash a plastic holding chamber with a detergent. However, such a solution can be cumbersome. Accordingly, the need remains for an improved holding chamber made of plastic, preferably clear, having inherent substantially permanent antistatic properties.

SUMMARY

By way of introduction, various preferred embodiments of an aerosol medication delivery apparatus include a holding chamber having an input end and an output end and defining an interior space. In one embodiment, the holding chamber is antistatic and is made of a plastic material having a surface resistivity of less than about 10E12 ohm/sq, and preferably between about 10E10 and about 10E12 ohm/sq. In one preferred embodiment, at least a portion of the holding chamber is see-through. In addition, the antistatic properties are substantially permanent.

In another embodiment, a component, separate from the holding chamber, is antistatic and is made of a material having a surface resistivity of between about 10E10 and about 10E12 ohm/sq. The component is connected, directly or indirectly, to the holding chamber, which may or may not be antistatic. In one preferred embodiment, the component is a backpiece connected to an input end of the holding chamber. In one embodiment, the backpiece is made of an elastomeric material. In another embodiment, the component includes a mouthpiece connected to the output end of the holding chamber.

In other aspects, various methods are provided that include introducing an aerosol into the holding chamber at the input end thereof and inhaling the aerosol through the output end.

The various embodiments provide significant advantages over other holding chamber devices. For example, both the holding chamber and component, such as the backpiece, can be made of various plastic and/or elastomeric materials, which are relatively light weight and inexpensive to manufacture. At the same time, one or more of the holding chamber and components can be made antistatic, such that the medication particles in the aerosol are less likely to be attracted to the interior surface of the holding chamber or components, thereby providing improved consistency in the amount of medication delivered to the patient without pretreating the delivery apparatus. In addition, the plastic material can be made see-through, such that the user or caretaker can monitor and visualize the interior of the holding chamber and/or component. Moreover, the antistatic properties are substantially permanent, such that they do not degrade over time.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 1 is a perspective view of a first embodiment of an aerosol medication delivery system.

FIG. 2 is an exploded perspective view of the aerosol medication delivery system shown in FIG. 1.

FIG. 3 is a side cross-sectional view of an alternative embodiment of a holding chamber.

FIG. 4 is a side cross-sectional view of an alternative embodiment of a medication delivery system.

FIG. 5 is a side cross-sectional view of an alternative embodiment of a medication delivery system.

FIG. 6 is an exploded perspective view of an alternative embodiment of a medication delivery system.

FIG. 7 is an exploded perspective view of an alternative embodiment of a medication delivery system.

FIG. 8 is an exploded perspective view of an alternative embodiment of a medication delivery system.

DETAILED DESCRIPTION OF THE PRESENTLY PREFERRED EMBODIMENTS

Figures 1, 2:
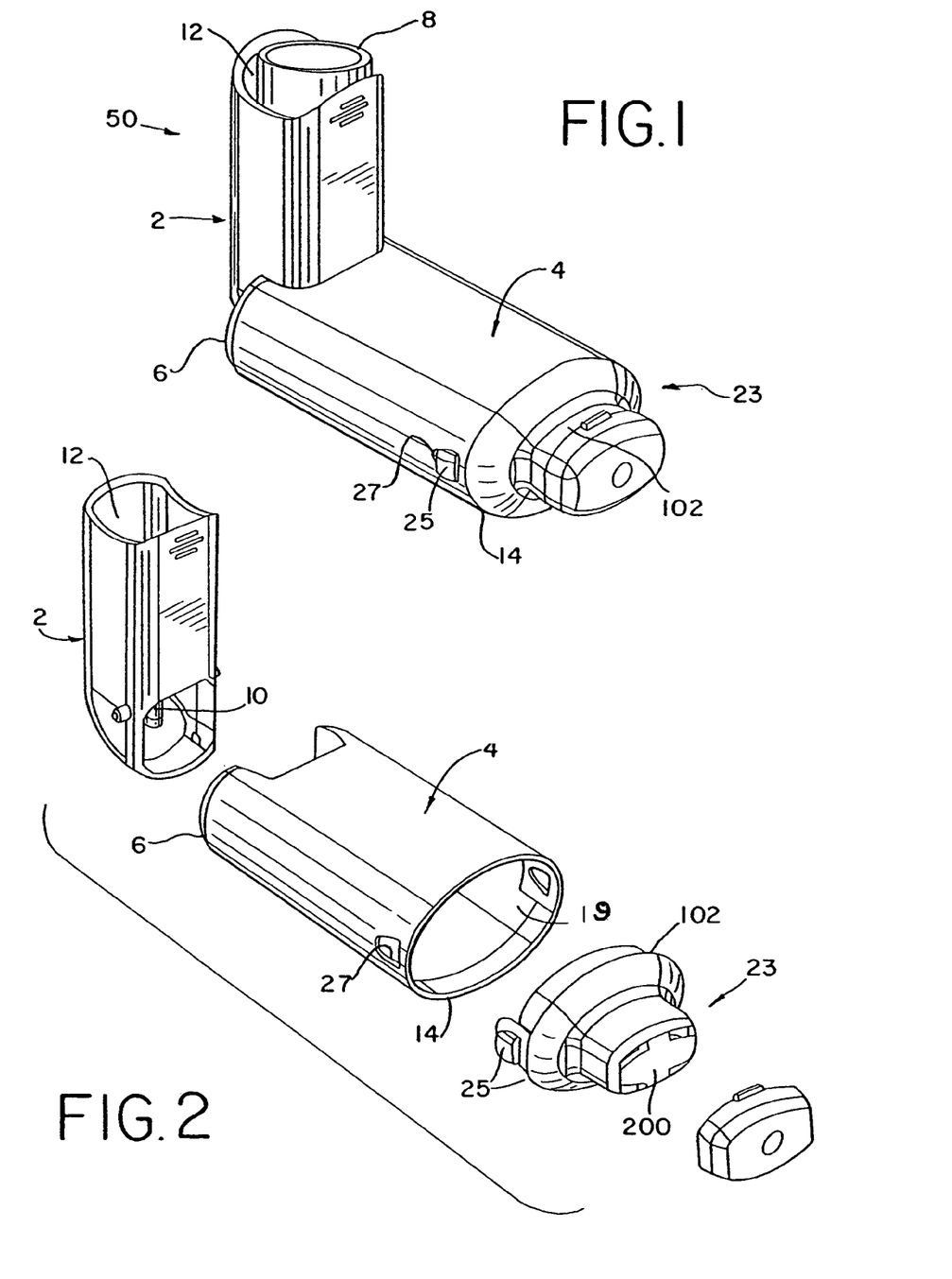
Figures 6, 7:
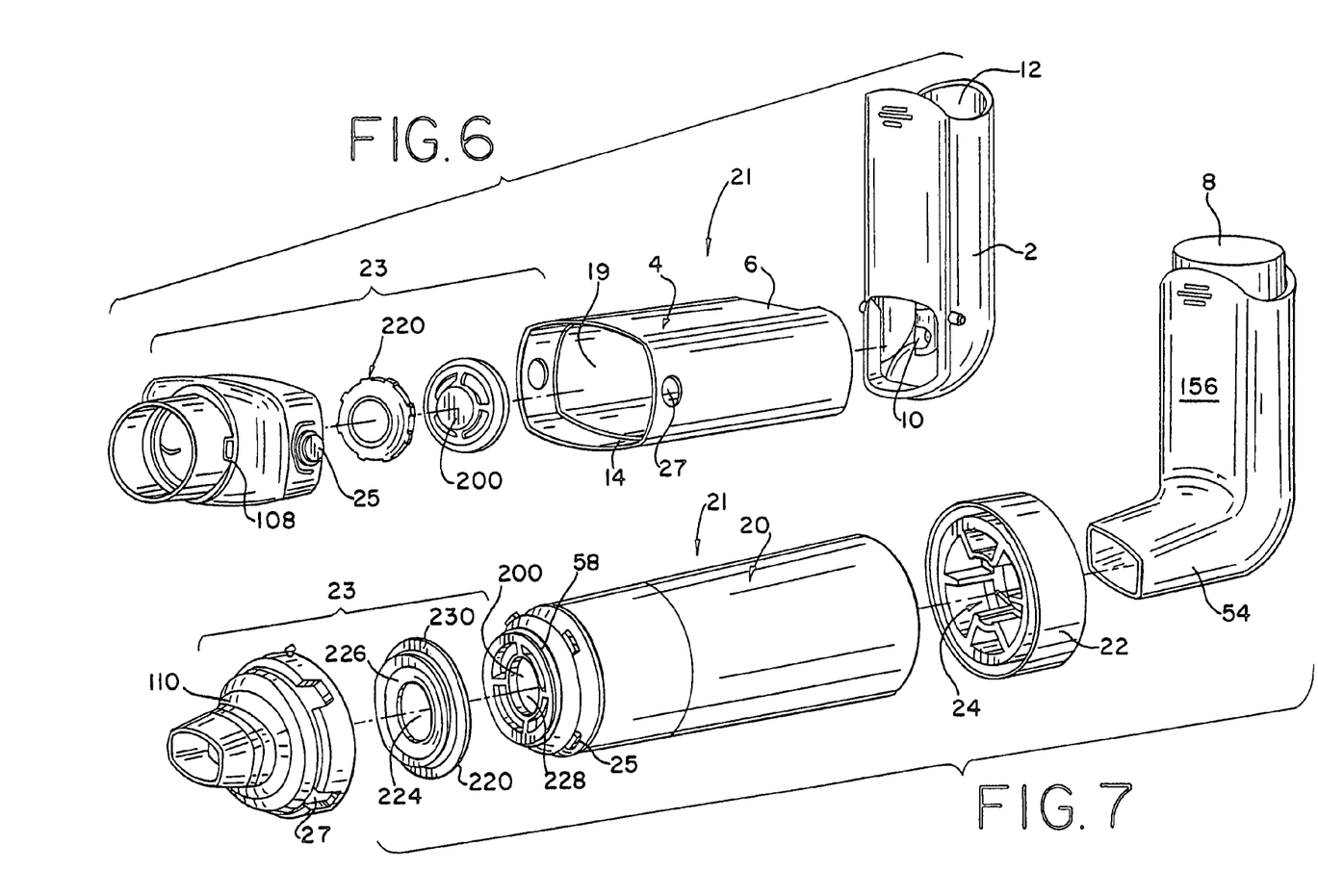

Referring to FIGS. 1, 2 and 6, one preferred embodiment of an aerosol medication delivery system 50 includes a pressurized metered dose inhaler (pMDI) holding portion 2, or dispenser (sometimes referred to as an actuator boot), coupled to a chamber housing 4, otherwise referred to as a holding chamber, at an input end 6 thereof. A medication container 8, for example a pMDI canister, is disposed in a cavity 12 formed in the dispenser, with a stem of the canister being inserted into a well 10 formed in the bottom of the dispenser. Preferably, the dispenser 2 is pivotally connected to the chamber housing 4 so that the dispenser 2 can be pivoted and translated for storage inside the chamber housing when the device is not in use. The term "medication" or "medicament" and variations thereof as used herein means any substance used in therapy, for example in the treatment of asthma.

In various alternative embodiments shown in FIGS. 3, 4 and 7-9, the apparatus includes a backpiece 22 secured to a holding chamber 20, 90 at an input end 52, 94 thereof. The backpiece 22, which is preferably formed as a separate component from the holding chamber, includes an opening 24 shaped to receive a mouthpiece portion 54 of a separate pMDI dispenser 156, which holds the container 8. Various configurations of chamber housings and dispensers are shown in U.S. Pat. Nos. 6,293,279, 5,012,803 and 5,012,804, the entire disclosures of which are hereby incorporated herein by reference. It should be understood that a holding chamber can also be used in conjunction with medication delivery containers other than a pMDI container, including for example and without limitation nasal sprayers, dry powder inhalers and nebulizer systems.

Figure 5:
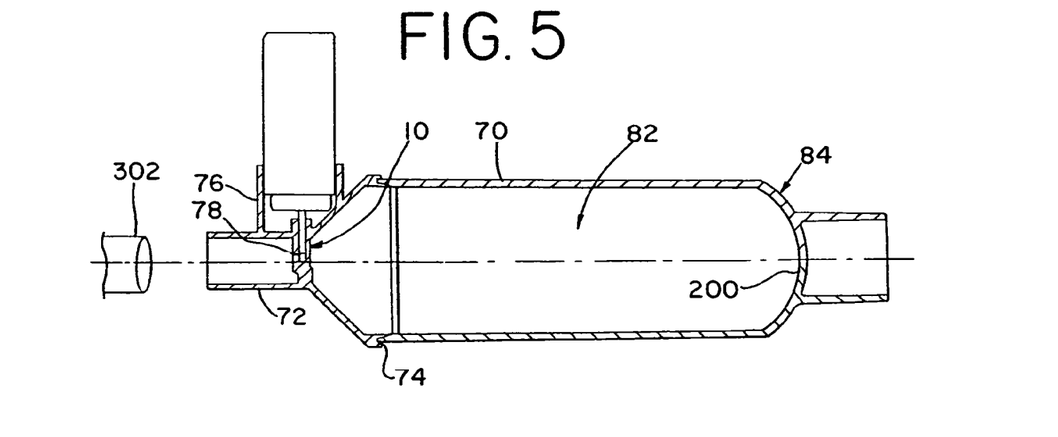

In yet another embodiment, shown in FIG. 5, the apparatus includes a holding chamber 70 that can be introduced into the inspiratory flow path of a ventilator circuit 302. The apparatus includes a backpiece member 72, configured with a pMDI receptacle 76, which is connected to the input end 79 of the holding chamber. The receptacle 76 is configured as a cylindrical housing shaped to receive the pMDI container and includes a well 10 formed at the bottom of the receptacle shaped to receive a pMDI valve stem 78. A discharge opening 80 is formed in the receptacle and communicates with the well 10, thereby allowing the aerosol, and medication, to be introduced into an interior 32 of the holding chamber through the backpiece 72 and input end 74 of the holding chamber.

Figure 9:
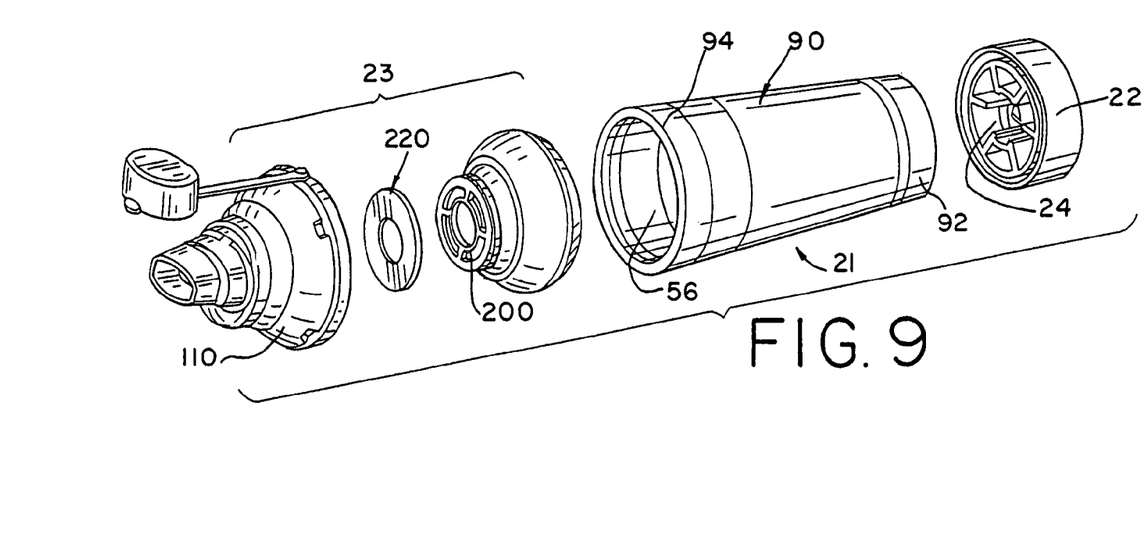
FIG. 9 is an exploded perspective view of an alternative embodiment of a medication delivery system.

In all of the embodiments, the chamber housing 4, 20, 70 defines an interior space 19, 56, 82 and further includes an output end 14, 58, 84, 94, through which the medication is dispensed to the user. The holding chamber 20 can have a substantially circular cross section as shown for example in FIG. 7, or the holding chamber 4 can have other shapes, for example a substantially oval cross-section as shown in FIG. 1 or an elliptical or rectangular cross-section (not shown). In addition, the holding chamber 20 can have a substantially constant cross-section, for example forming a cylinder as shown in FIG. 7, or the holding chamber 20 can be tapered, such that the cross-sectional area gradually increases from the input end 92 to the output end 94 as shown in FIGS. 8 and 9, or decreases along the same path (not shown).

Figure 3:
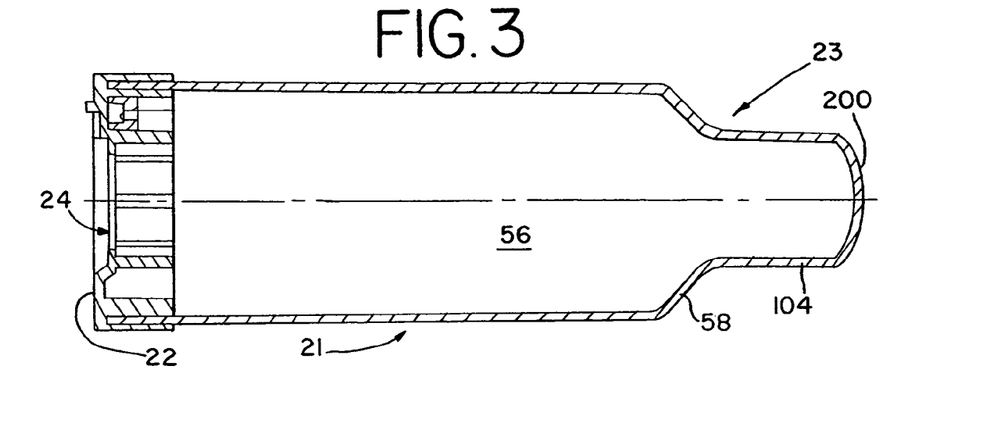
Figure 4:
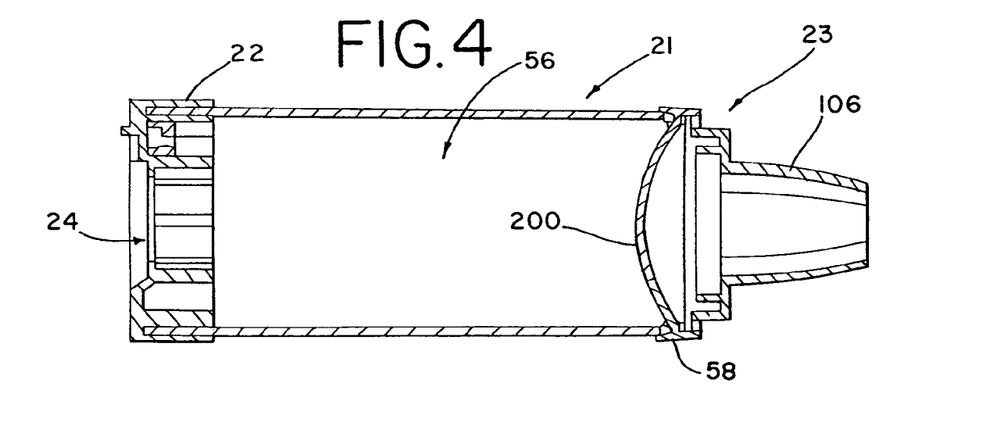

As shown in the embodiments of FIGS. 1-3 and 6-8, the output end 14, 58, 84, 94 includes a downstream portion 23 that is configured with a mouthpiece 102, 104, 106, 108, 110. The mouthpiece 102, 106, 108, 110 can be formed as a separate component that is releasably secured to a main housing 21 with one or more fastening elements 25, 27, as shown for example in FIGS. 1, 2, and 4-8. For example, the fastening elements can be configured as tabs 25 and recesses 24 in one preferred embodiment, which provides a snap-fit between the main housing 21 and the downstream portion 23. As shown in FIG. 3, the mouthpiece 104 can alternatively be formed integrally with the housing.

The term "component" as used herein means any part, member, device, or feature that forms part of the medication delivery apparatus, and includes without limitation, the chamber housing, the backpiece, the mouthpiece, the output end, various adapters, baffle members, actuators, valve assemblies, tubes or conduits, masks, and the like, and portions thereof, which are incorporated into the system. The terms "connected" and "secured," and variations thereof, as used herein, means that one or more members are associated or coupled to each other, either directly or indirectly (for example with intervening members).

Figure 10:
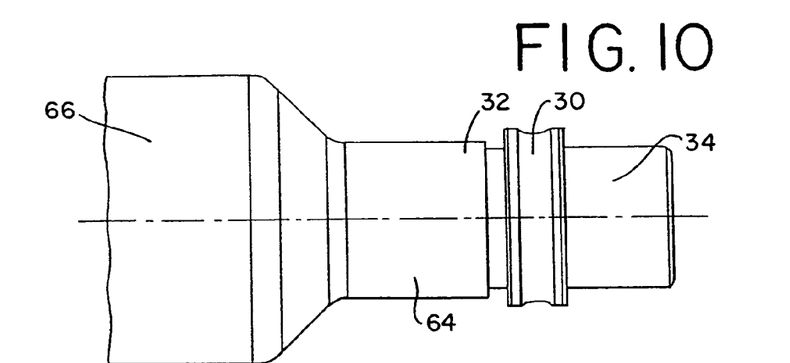
FIG. 10 is a partial side view of an output end of an alternative embodiment of a holding chamber.

In one alternative embodiment, shown in FIG. 10, an adapter 30 includes an input end 32 configured as an insert portion that is fitted in an opening formed in an output end 64 of a chamber housing 66. Conversely, the input end 32 can be fitted over or around an end portion of the chamber housing. In one embodiment, the adapter includes a narrow orifice, as disclosed for example in U.S. Provisional Patent Application Ser. No. 60/377,528, filed May 3, 2002 and entitled "Aerosol Medication Delivery Apparatus With Narrow Orifice," the entire disclosure of which is hereby incorporated herein by reference. The adapter further includes an output end 34 that, in one preferred embodiment, is shaped to be received in the mouth of the user. For example, the output end 34 can have an outer circular cross-section, or it can be elliptical, oval, obround or any other shaped suitable for insertion into the mouth of the user. Alternatively, an additional mouthpiece (not shown) can be fitted in or around the output end.

In yet another alternative embodiment, shown in FIG. 9, a mask 160 is fitted in or around, i.e. a connector member 300, secured to the output end of the holding chamber. The mask 160 is shaped to be disposed over the face, preferably including the mouth and nose, of the user. In yet another alternative embodiment, a nasal applicator (not shown), provided for example with prongs, can be fitted into or around the output end. In yet another embodiment, a patient interface element, such as an endotracheal tube, can be fitted to one or more of the output end of the holding chamber or adapter.

In all of the embodiments, shown for example in FIGS. 1-9, the output end 14, 58, 84, 94 of the holding chamber 4, 20, 70, 90 can be configured with a baffle member 200. The baffle member 200 is preferably curved, and can have one or more concave or convex surfaces facing toward and away from the input end of the holding chamber. Of course, it should be understood that the baffle member 200 can be flat, or have other non-curved shapes. In addition, it should be understood that the apparatus can be configured without a baffle formed at the output end of the holding chamber.

As shown in FIGS. 6-9, the output end of the holding chamber can be configured with one or both of an inhalation and exhalation valve 220. In one embodiment, shown in FIG. 7, the valve 220 includes a central open area 224 having a peripheral edge portion 226 that seats on a valve seat formed on a center baffle portion 228 of the baffle member 200. The valve is displaced from the seat during inhalation. An outer peripheral portion 230 of the valve is seated on a second valve seat and is displaced therefrom during exhalation. Of course, it should be understood that other valve configurations, such as a duckbill valve, can also be used.

The valve member 220 is preferably made of a flexible material, including for example and without limitation a silicone, a thermoplastic elastomer, rubber, Ethylene-Propylene-Diene-Monomer (EPDM) or Berfluodelaastomers (FFKN).

Preferably, the adapter 30 and the chamber housing 4, 20, 70, 90 are made of a hard antistatic plastic, for example by injection molding. Typically, plastics have a surface resistivity of greater than 10E12 ohm/sq. Antistatic materials have a surface resistivity of between about 10E10 ohm/sq and about 10E 12 ohm/sq. Static dissipative materials have a surface resistivity of between about 10E6 ohm/sq. and about 10E12 ohm/sq. Conductive materials have a surface resistivity of between about 10E1 ohm/sq and about 10E6 ohm/sq. Metals typically have a surface resistivity of between about 10E-1 to about 10E-5 ohm/sq. Surface resistivity as set forth herein is measured pursuant to ASTM test D257.

In various embodiments, the chamber housing 4, 20, 70, 90, adapter 30, mouthpiece 102, 106, 108, 110, and/or backpiece 22, 72 are made of one or more of a polypropylene, polycarbonate, polystyrene, nylon, ABS, high density polyethylene (HDPE), acetal, PBT, PETG, various thermoplastic elastomers, and/or combinations thereof. For example, the components can be made of various PermaStat® compounds available from the RTP Company, having a place of business at 580 East Front Street, Winona, Minn., 55987. Of course, it should be understood that materials other than PermaStat® compounds are suitable. In any event, the materials preferably have a surface resistivity of less than about 10E12 ohm/sq, more preferably between about 10E1 and about 10E12 ohm/sq, more preferably between about 10E6 and about 10E12 ohm/sq, more preferably between about 10E10 and about 10E12 ohm/sq, and most preferably between about 10E10 and about 10E11 ohm/sq.

In various exemplary embodiments, and without limitation, the chamber housing 4, 20, 70, 90, adapter 30, mouthpiece 102, 106, 108, 110, and backpiece 22, 72 can be made from one or more of a PermaStat® 100 series polypropylene material, a PermaStat® 200 series Nylon (PA6, PA6/6 or P12) material, a PermaStat® 300 series polycarbonate material, a PermaStat® 400 series polystyrene (PS) material, a PermaStat® 600 series Acrylonitrile Butadiene Styrene (ABS) material, a PermaStat® 700 series high density polyethylene (HDPE) material, a PermaStat® 800 series Acetal (POM) material, a PermaStat® 1000 series polybutylene Terephthalate (PBT) material, a PermaStat® 1100 series polyethylene Terephthalate Glycol modified (PETG) material, a PermaStat® 1200 series polyurethane thermoplastic elastomer material, a PermaStat® 1500 series polyester thermoplastic elastomer, a PermaStat® 1800 series acrylic (PMMA) material, a PermaStat® 2500 series polycarbonate/ABS alloy material, a PermaStat® 2700 series Styrenic thermoplastic elastomer (TES) material, a PermaStat® 2800 series Olefinic thermoplastic elastomer (TEO) materials, or a PermaStat® 4700 series polytrimethylene Terephthalate (PTT) material, all being permanently antistatic and having a surface resistivity between about 10E10 and about 10E11 ohms/sq with electrical shock discharge (ESD) protection. PermaStat® compounds are colorable and retain the transparency of the host resin. Such compounds are further free of carbon black, and are non-sloughing, meaning they do not release conductive contaminants. The compounds are further formulated to meet MIL-PRF-81705D static decay requirements. Since the compound is compounded into the molded material, the component is more robust and can function in all humidity levels. The term "plastic" as used herein includes thermoplastic elastomer materials.

Preferably, the chamber housing 4, 20, 70, mouthpiece 102, 106, 108, 110 and adapter 30 are made of an RTP 199 X 95281 S Nat/Clear, available from the RTP Company. Another suitable material is the RTP 199 X 95281 U Nat/Clear material, which is a high temperature material, also available from RTP Company.

Preferably, the backpiece 22, 72 is made of one or more of the elastomeric materials, or other elastomers available from RTP, including for example the RTP 1200 series Polyurethane elastomers, the 1500 series copolyester elastomers, the 2700 series styrenic elastomers and/or the 2800 series olefinic elastomers. It should be understood that the backpiece 22, 72 also can be made of non-elastomeric materials. In addition, it should be understood that the holding chamber 4, 20, 70, 90, and various components, including without limitation, the adapter, mouthpiece and backpiece can be made of materials that are not antistatic, having for example surface resitivities of greater than 10E12 ohm/sq. Therefore, for example, the delivery apparatus may be configured with only the holding chamber 4, 20, 70, 90 being antistatic, only one or more of the various components being antistatic, such as the backpiece, mouthpiece and/or adapter but not the holding chamber, or all of the components including the holding chamber being antistatic.

Preferably, the antistatic material is substantially clear, such that at least a portion of the various components, including without limitation the holding chamber, backpiece, mouthpiece and adapters, are see-through such that the user can monitor the interior of the delivery apparatus. In this way, the term "clear" simply means see-through, and includes materials that are completely transparent, as well as materials that are opaque or shaded, so long as an object is visible on the other side of the material. For example, by providing one or more see-through components, various visual flow indicators can be seen. Such visual indicators are shown for example in U.S. Provisional Application 60/382, 227, filed May 21, 2002, the entire disclosure of which is hereby incorporated herein by reference. In addition, the antistatic properties associated with various afore-described materials are substantially permanent, and will not dissipate over time.

In other embodiments, the holding chamber 4, 20, 70, 90, and other components, including for example and without limitation the adapter 30, mouthpiece 102, 106, 108, 110 and backpiece 22, 72, are made of various thermoplastics using various levels of additives, including without limitation, stainless steel fibers, carbon fibers and carbon powder. It should be understood that an antistatic coating also can be applied to the chamber housing and components, such as the adapter, mouthpiece and backpiece to achieve the desired resistivities.

In operation, the user actuates the dispenser 2, 156 or other device, so as to discharge a medication, preferably in aerosol form, through the input end 6, 52, 74 and introduce the medication into the interior space 19, 56, 82 of the holding chamber 4, 20, 70, 90, or chamber housing. The medication is thereafter delivered to the user, for example by inhalation through the output end 14, 58, 84 of the holding chamber, by way of one or more of a mouthpiece, mask or endotracheal tube. The antistatic properties of the holding chamber and backpiece reduce the likelihood that the medication particles will be attracted thereto.

Referring to FIGS. 10-15, exemplary powder medication delivery systems, or dry powder inhalers 400 are shown. Each inhaler 400 includes a holding chamber 402 and a mouthpiece 408. The inhaler shown in FIGS. 14 and 15, further includes a visual flow indicator 412 mounted within a viewing port area 410. The flow indicator moves within the port area to provide a visual cue to the patient or caretaker that the inhalation flow is adequate to properly administer the medication to the patient. Various aspects of the inhaler are further disclosed and shown in U.S. Provisional Patent Application Ser. No. 60/382,227, filed May 21, 2002, the entire disclosure of which is hereby incorporated herein by reference.

Figures 11, 12, 13:
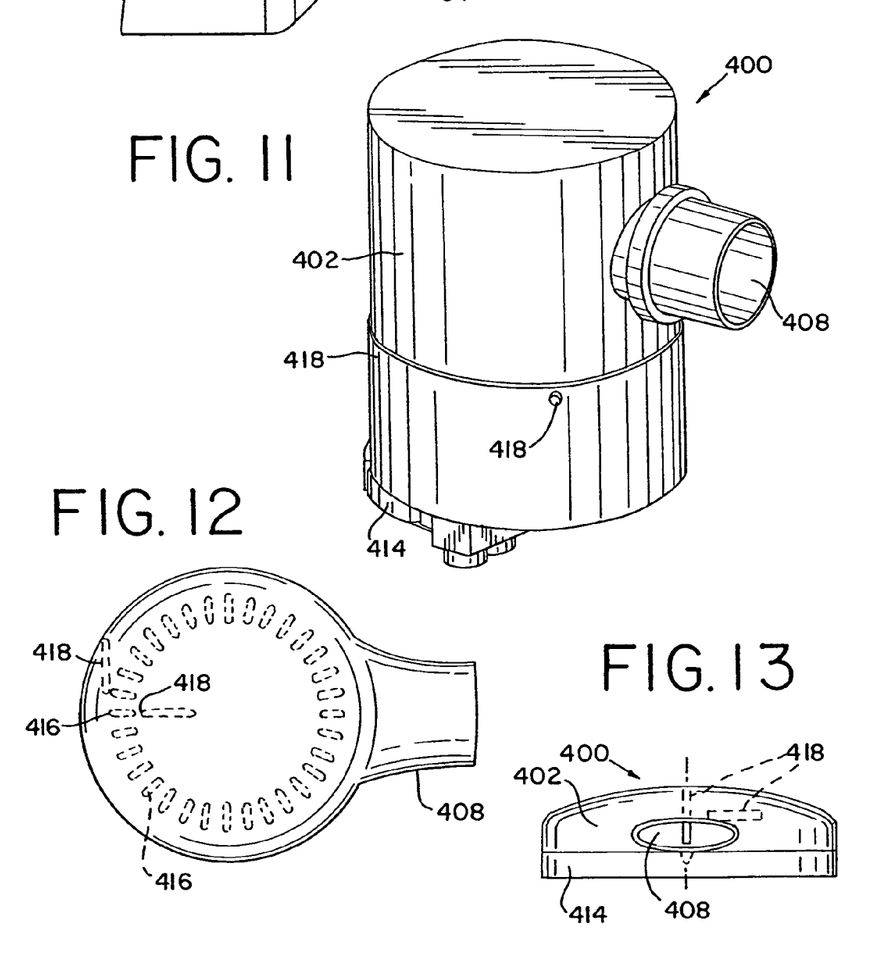
FIG. 11 is a perspective view of one embodiment of a dry powder inhaler.
FIG. 12 is a top view of an alternative embodiment of a dry powder inhaler.
FIG. 13 is an end view of the dry powder inhaler shown in FIG. 12.
Figure 14:
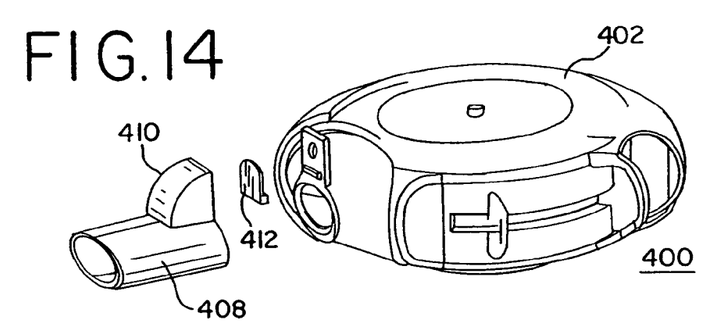
FIG. 14 is an exploded perspective view of an alternative embodiment of a dry powder inhaler.
Figure 15:
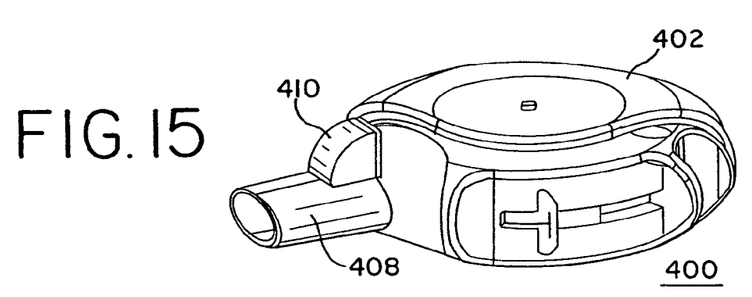
FIG. 15 is a perspective view of the dry powder inhaler shown in FIG. 14.

Referring to the inhaler in FIGS. 11-13, the inhaler 400 includes a holding chamber 402 and a mouthpiece 408, which can be separate from (FIG. 11) or integral with (FIGS. 12-13) the holding chamber. The inhaler further includes a medicament holding cassette 414, which has a plurality of holding portions 416 that hold a plurality of dose of medication, each of which can be subsequently exposed to the interior of the holding chamber. One or more air entry passageways 418 are directed at the holding portions 416 and fluidize the medication within the holding chamber, wherein it can be subsequently inhaled through the mouthpiece. Various aspects of the inhaler are further disclosed and shown in U.S. Pat. No. 6,116,239, the entire disclosure of which is hereby incorporated herein by reference.

It should be understood that any or all of the various components of the inhalers 400, including the holding chambers 402, mouthpieces 408, air intake passageways 418, cassettes 414, and/or holding portions 416, can be made of one or more of the various antistatic materials described herein.

Figure 16:
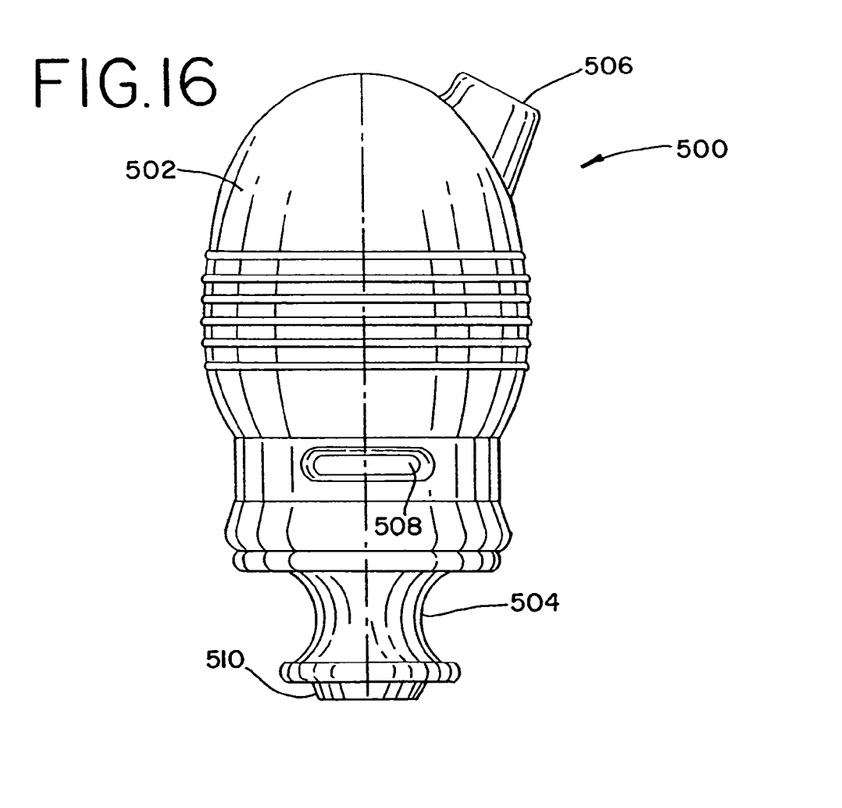
FIG. 16 is a side view of a nasal inhaler.

Various nasal inhalers 500, an example of which is shown in FIG. 16, may also include one or more of a holding chamber 502 having an input end 510 and an output end formed as an outlet 506, an actuator (not shown) and an adapter 504, one or more of which may be made of the various antistatic materials described herein. One or more inlet valves 508 may be provided in the holding chamber 502. Various exemplary nasal inhalers and applicators are disclosed for example in U.S. patent application Ser. No. 09/834,037, filed Apr. 11, 2001, and U.S. patent application Ser. No. 10/121,931, filed Apr. 12, 2002, the entire disclosures of which is hereby incorporated herein by reference.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A medication delivery apparatus comprising:
   an antistatic holding chamber comprising a plastic material having a surface resistivity of between about 10E10 and about 10E12 ohm/sq, wherein said holding chamber has an input end and an output end spaced apart along a longitudinal axis;
   a patient interface component connected to said output end and comprising an interior surface defining a flow passage; and
   a one-way valve disposed adjacent said output end, said one-way valve moveable between an open position and a closed position, wherein said one-way valve has a central opening when in said open position, said central opening defining a flow path along said longitudinal axis, wherein no portion of said interior surface of said patient interface component downstream of said one-way valve intersects said flow path in an orthogonal relationship.

2. The apparatus of claim 1 wherein said plastic material comprises a polypropylene material.

3. The apparatus of claim 1 further comprising a backpiece separate from said holding chamber and comprising an elastomeric material having a surface resistivity of between about 10E10 and about 10E12 ohm/sq, wherein said backpiece is connected to said input end of said holding chamber.

4. The apparatus of claim 3 wherein said backpiece comprises an opening formed therethrough, said opening shaped and adapted to receive a portion of a pressurized metered does inhaler.

5. The apparatus of claim 1 wherein said material is selected from the group consisting of polypropylene, polycarbonate, polystyrene, nylon, acrylonitrile butadiene styrene, high density polyethylene, acetal, polybutylene terephthalate, and polyethylene terephthalate glycol.

6. The apparatus of claim 1 wherein at least a portion of said holding chamber is see-through.

7. The apparatus of claim 1 wherein said surface resistivity of said plastic material is between about 10E10 and about 10E11 ohm/sq.

8. The apparatus of claim 1 further comprising a second antistatic component separate from said holding chamber and comprising a material having a surface resistivity of between about 10E10 and about 10E12 ohm/sq, and wherein said second antistatic component is connected to said holding chamber.

9. The apparatus of claim 8 wherein said second antistatic component comprises said patient interface component connected to said output end of said holding chamber.

10. The apparatus of claim 8 wherein said second antistatic component comprises a backpiece connected to said input end of said holding chamber.

11. The apparatus of claim 10 wherein said backpiece comprises an elastomeric material.

12. The apparatus of claim 10 wherein said backpiece comprises an opening formed therethrough, said opening shaped and adapted to receive a portion of a pressurized metered dose inhaler.

13. The apparatus of claim 10 wherein said material comprises a thermoplastic elastomer material.

14. The apparatus of claim 8 wherein said material of said second antistatic component is selected from the group consisting of a polyurethane elastomer, polyester elastomer, styrenic elastomer and olefinic elastomer.

15. The apparatus of claim 8 wherein at least a portion of said holding chamber and said second antistatic component is see-through.

16. The apparatus of claim 1 wherein said patient interface component comprises a mouthpiece.

17. The apparatus of claim 16 wherein said interior surface of said mouthpiece is not antistatic.

* * * * *

UNITED STATES PATENT AND TRADEMARK OFFICE
CERTIFICATE OF CORRECTION

PATENT NO.         : 7,360,537 B2                                    Page 1 of 1
APPLICATION NO.    : 10/821260
DATED              : April 22, 2008
INVENTOR(S)        : Sarah Bruce Snyder et al.

It is certified that error appears in the above-identified patent and that said Letters Patent is hereby corrected as shown below:

On the Title Page

On page 2, Item (56), line 20, under "OTHER PUBLICATIONS", delete "http://222.rtpcompany.com" and substitute --http://www.rtpcompany.com-- in its place.

In column 8, in claim 4 , line 4, after "metered" delete "does" and substitute --dose-- in its place.

Signed and Sealed this

Sixteenth Day of December, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,360,537 B2 | Page 1 of 1 |
| APPLICATION NO. | : 10/821260 | |
| DATED | : April 22, 2008 | |
| INVENTOR(S) | : Sarah Bruce Snyder et al. | |

It is certified that error appears in the above-identified patent and that said Letters Patent is hereby corrected as shown below:

On the Title Page

On page 2, Item (56), line 20, under "OTHER PUBLICATIONS", delete "http://222.rtpcompany.com" and substitute --http://www.rtpcompany.com-- in its place.

In column 8, in claim 4, line 42, after "metered" delete "does" and substitute --dose-- in its place.

This certificate supersedes the Certificate of Correction issued December 16, 2008.

Signed and Sealed this

Thirteenth Day of January, 2009

JON W. DUDAS
*Director of the United States Patent and Trademark Office*